United States Patent [19]

Spina et al.

[11] 4,135,516
[45] Jan. 23, 1979

[54] DELIVERY APPARATUS AND METHOD FOR TREATMENT OF INTRALENTICULAR CATARACTS WITH EXOGENOUS ENZYMES

[75] Inventors: Joseph Spina, Bryn Mawr, Pa.; Michael K. Weibel, Redding, Conn.

[73] Assignee: Novo Laboratories, Incorporated, Wilton, Conn.

[21] Appl. No.: 771,572

[22] Filed: Feb. 24, 1977

Related U.S. Application Data

[63] Continuation-in-part of Ser. No. 660,873.

[51] Int. Cl.² .............................................. A61F 9/00
[52] U.S. Cl. .............................................. 128/303 R
[58] Field of Search .................. 128/276, 303 R, 305, 128/213, 214 F, 215, 230

[56] References Cited
U.S. PATENT DOCUMENTS

| | | | |
|---|---|---|---|
| 3,347,235 | 10/1967 | Hunnicutt | 128/276 |
| 3,589,363 | 6/1971 | Banko et al. | 128/303 R |
| 3,815,604 | 6/1974 | O'Malley et al. | 128/305 |
| 3,994,297 | 11/1976 | Kopf | 128/305 |
| 4,033,349 | 7/1977 | Baehr | 128/303 R |

Primary Examiner—William E. Kamm
Attorney, Agent, or Firm—Fidelman, Wolffe & Waldron

[57] ABSTRACT

An enzymatic intralenticular cataract treatment method for removal of nuclear cortical and subcapsular regions of the cataractous lens through enzymatic digestion thereof, which comprises introduction of a concentrated solution of proteinase into the nuclear and cortical regions of a cataractous lens by way of a cannula inserted through a very tiny incision in the cornea and puncture opening into the lens capsule, leaving all other structures within the eye intact, after which a gas bubble is introduced from the cannula into the lens, the gas bubble serving to maintain the enzyme compartmentalized within the subcapsular region.

As illustrated in FIG. 4, a preferred embodiment of the apparatus involved with the method comprises an enzyme reservoir connected through a delivery means and a four port, two channel valve to a cannula. The cannula is filled with enzyme solution then the delivery means and valve are operated by the surgeon so as to carry out the above described treatment method.

9 Claims, 4 Drawing Figures

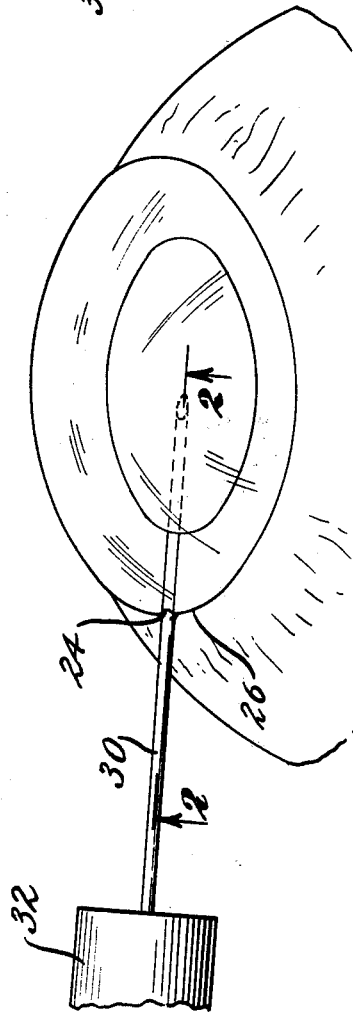
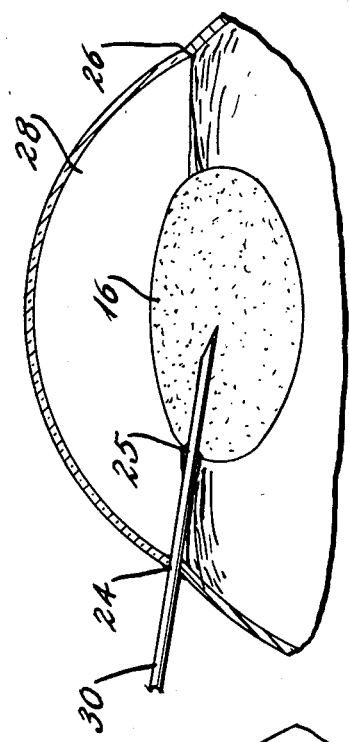
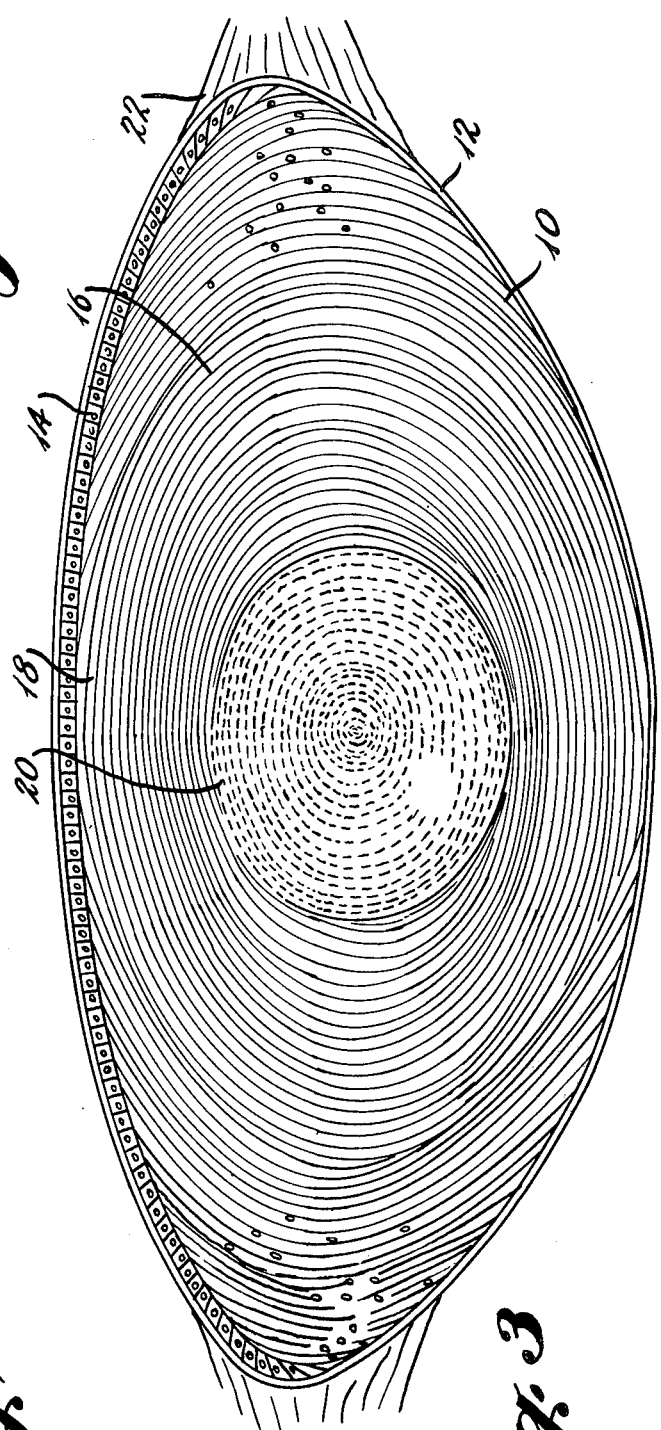

DELIVERY APPARATUS AND METHOD FOR TREATMENT OF INTRALENTICULAR CATARACTS WITH EXOGENOUS ENZYMES

This application is a continuation-in-part of Ser. No. 660,873 filed Feb. 24, 1976, now U.S. Pat. No. 4,078,564.

BACKGROUND OF THE INVENTION

I. Field of the Invention

This invention lies in the field of cataract surgery and in particular relates to the enzymatic treatment of cataracts followed by removal of the enzymatically digested cataractous material.

II. Background

The lens is an optically-clear, encapsulated disc-like structure which is suspended within the eye, behind the iris and in front of the vitreous. It supplies part of the optical refracting power of the eye. The lens becomes cataractous when its nuclear and/or cortical and/or subcapsular regions become opaque, thus blocking the path of light entering the eye, thereby causing diminished vision. A cataract is simply a lens that has become cloudy.

For further background to this invention and for more detailed discussion of the rationale of liquefying a lens enzymatically, reference is made to copending Ser. No. 771,550 now abandoned, filed concurrently herewith (also a continuation-in-part of application Ser. No. 660,873 filed Feb. 24, 1976). Suffice it to point out here that surgical techniques for removing cataracts are not entirely satisfactory to patient and surgeons.

The object of this invention is to provide an operating procedure which eliminates much, if not all, of the hazards and trauma involved in the heretofore known surgical procedures for removing cataracts.

A further object of this invention is to provide a system for delivering a lens digesting enzyme to the lens and for subsequently maintaining the enzyme compartmentalized within the subcapsular region.

SUMMARY OF THE INVENTION

This invention provides a procedure and apparatus for intralenticular cataract therapy which involves dispersing a concentrated solution of exogenous proteinase throughout the nuclear, cortical and subcapsular regions of a cataractous lens through a puncture opening, and thereafter sealing the opening with a gas bubble.

RATIONALE OF THE INVENTION

The invention takes advantage of a unique physiological situation within the lens itself. During the embryonic stages of human development, the lens material is isolated from the rest of the body and develops independent of the organism as a whole to such an extent that every human will react to the contents of his or her lens as if it were a foreign protein. In the adult human, the lens is surrounded by the lens capsule which is primarily collagen; and this capsule actually isolates the lens from the body to such an extent that exogenous proteins, e.g., enzymes, may be introduced into the lens without creating immunologic foreign protein responses thereto.

Technological advances have made available to the surgeon both equipment and techniques for operating on the lens itself. Conventional surgical equipment, including for example the operating microscope, that has gone into widespread use in the past fifteen years now enables the surgeon to see details that previously were too small for visualization. In addition, the availability of micro cannulae make it possible for a surgeon to enter a structure as small as the human lens (approximately 9 mm in diameter) without doing major damage thereto. In total, the operating techniques and the surgical equipment required for surgery on the lens itself already available to the art, can be modified readily for practice of this invention.

Within the art of surgical ophthalmic intraocular procedures for conventional cataract removal, the use of an exogenous enzyme to facilitate the removal of an intact lens is established. A well characterized proteolytic enzyme, α-chymotrypsin, has been used to soften the suspensory ligaments of the zonular region which attach the lens capsule to the ciliary muscle.

Also the use of an exogenous enzyme, fibrinolysin, to degrade blood clots within the eye is established within the art of ophthalmic intraocular surgery.

Furthermore, there is an established precedent in the medical arts for use of digestive enzymes as an aid in necrotic tissue removal for wound debridement procedures.

In the treatment of congenital cataracts, too firm to be aspirated using a simple needle and syringe, some eye surgeons have believed for years that incision of the anterior capsule permits the enzymes of the aqueous humor to enter the firm nucleus; and then within a few days, the cataract softens to the extent that it can be aspirated easily. This procedure does not work for hard, senile cataracts because of the low peripheral permeability associated with their compact nature.

It has now been discovered that senile cataracts can be treated by proteinases, so as to soften the lens sufficiently to allow its removal by aspiration and irrigation techniques. For a more detailed discussion of cataract removal by enzymatic liquefaction, reference is made to Ser. No. 771,550 now abandoned filed concurrently herewith (which application also is a continuation-in-part of Ser. No. 660,873 filed Feb. 24, 1976, now U.S. Pat. No. 4,078,564.

EXPLANATION OF THE INVENTION

For further understanding of this invention, reference is now made to the attached drawing, wherein:

FIG. 1 diagrammatically illustrates a cannula inserted in the lens of an eye;

FIG. 2 is a cross-section taken along line 2—2 of FIG. 1;

FIG. 3 is an enlarged diagrammatic cross-section of the human lens capsule and its contents.

Figure 4:
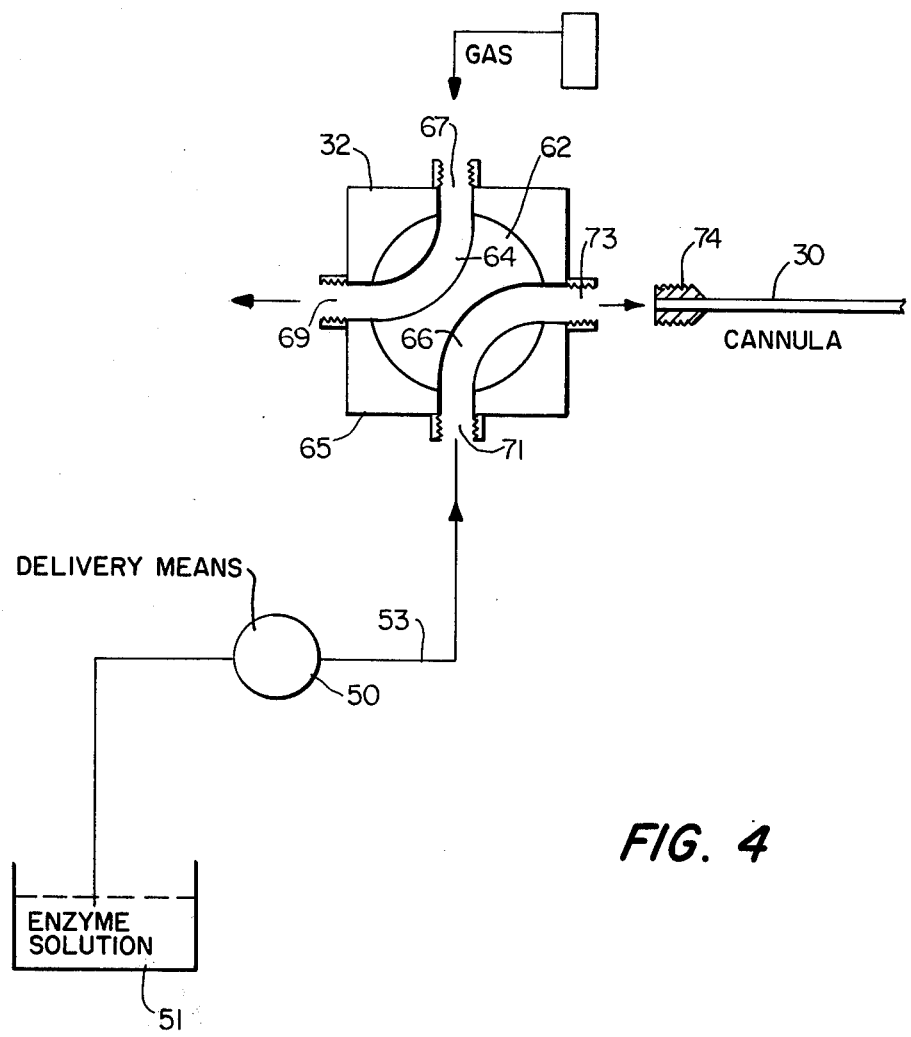
FIG. 4 is a diagrammatic illustration of the apparatus for supplying enzyme solution and then a gas bubble to the lens.

Referring now to FIG. 3, it may be seen how the lens 10 is divided up into capsule 12, epithelium 14 and lens substance 16 which consists of lens fiber. The lens substance can be further described as made up of the cortex 18, the cortex being a layer of soft, young superficial fibers which lie directly beneath the capsule 12, and the nucleus, the nucleus 20 being the hard, closely packed cells at the center of the lens. Extending into lens 10 at the sides thereof are the zonules 22, the zonules being the suspensatory ligaments which retain the lens in place inside the eye.

Any exogenous material inserted into the lens can be physically compartmentalized within the lens substance 16 by the lens capsule 12, provided the material does not act to destroy or rupture the lens capsule. If the opening made for insertion of the material is sealed, such material can be made to remain within the lens capsule 12 for an extended period of time. Significant to practice of this invention is that lens capsule 12 has a biochemical composition which is substantially different from that of cortex 18 and nucleus 20 of the main lens substance. Exogenous enzymes that are capable of selectively digesting the tissue of nucleus and cortex yet leave lens capsule 12 whole exist. Parenthetically, it may be noted that the macromolecular character of enzymes keeps them from permeating rapidly, if at all, through the reticular structure of the capsular membrane. Accordingly, selective enzymes introduced into the cortex and nucleus will become trapped therein, and over a period of time are capable of enzymatically degrading the senile lens substance.

One exemplary mode of practicing the invention involves making a puncture 24 at the sclera or at the scleral-corneal juncture 26 large enough for a needle, as is illustrated in FIG. 1, followed by introduction of a concentrated solution of exogenous enzymes. Thereafter the opening is sealed by a gas bubble, e.g., an air bubble, and then sufficient time is allowed for enzymatic digestion of the lens. Subsequently, the liquefied lens is removed by conventional aspiration and irrigation techniques, employing for example the techniques described in the medical literature for removing congenital or soft cataracts.

As can be seen in FIG. 3, nucleus 20 and cortex 18, which completely fill the lens capsule, are layered (somewhat like an onion) so that any enzyme containing liquid forced into the lens substance 16 permeates the entire lens largely along the layer lines. In terms of practicing this invention, the layered structure places vitually all of the cells in the nucleus and cortex into immediate contact with the enzymes in the liquid. A normal senile cataract will accommodate up to 20 microliters of liquid without increasing the intraocular pressure to a level where rupture of the capsule 12 occurs. Accordingly, introduction of a concentrated solution of exogenous enzymes directly into the lens according to practice of this invention focuses an enzymatic action exclusively upon cortical, nuclear and subcapsular cataractous material in vivo.

Degrading the cataract in situ, as is herein contemplated, imposes requirements for high levels of enzymatic unit activity and of selectivity. Fortuitously, highly selective enzymes exist. With high purity forms of enzymes, such as for example crystalline enzymes, concentrated (aqueous) solutions of mixed enzymes can be formulated, for example 10% wt/wt solutions. Accordingly, the above-described 20 microliter limit allows introduction of as much as 2 mg of pure enzyme into the lens substance. Since a normal lens will weigh about 200 mg, the enzyme to substrate ratio of about 1:100, readily obtainable, constitutes a high enzyme:substrate ratio, particularly since the layered nature of the lens places virtually all of the lens cells into essentially direct contact with the enzyme solution. Because a gas bubble serves to seal the puncture opening against loss of enzyme solution from the lens capsule, the enzyme remains compartmentalized within the capsule. The exogenous enzyme will become deactivated within a few days; and by then, the (softened or liquefied) cataractous lens is ripe for removal.

DETAILED PRACTICE OF THE INVENTION

The detailed practice of this invention can be appreciated in light of the drawing, notably of FIGS. 1 and 2. As can be seen therein, the lens degrading solution is delivered by a microcannula 30 attached to a suitable miniaturized liquid dispensing device, such as a microliter four port valve 32 from a scleral or scleralcorneal juncture puncture directly into nucleus 20, introducing for example 15 microliters of a 5% wt/wt enzyme solution. The outside diameter of the microcannula, for example, may be approximately 200 microns or as small as structural strength considerations permit. (The tip may be electronically tapered). Large diameter cannulas tend to rent and/or rip the lens capsule during penetration thereof, and substantially smaller diameter cannulas do not possess sufficient rigidity to cleanly penetrate into the lens substance. Use of a tracked micromanipulator to reduce lateral motion of the cannula upon entering the lens is recommended but is not considered essential. With the aid of an operating microscope, a 200 micron microcannula can be adequately inserted into the center of the lens manually. (Complete restriction of lateral motion by the cannula once positioned in the lens is essential, however, for maintaining a good gas bubble seal within the needle track).

As has already been pointed out, the enzyme containing solution injected into the lens by a manual or pneumatic driven syringe system is an amount of fluid which can be accommodated by an average human lens, i.e. not more than about 20 microliters, and, e.g., only 6 microliters. The distribution pattern of the injected fluid may be observed by incorporating a soluble, inert dye such as dichloroindophenol or a fluorescent dye such as fluorescein into the injection fluid.

Injection of the solution into the central portion of the lens is followed by injection of a tiny gas bubble into the track of the cannula as the cannula is withdrawn from the lens and out of the eye. This tiny air bubble serves to seal the small puncture site 25 in the lens capsule and, thus, to block the egress of enzyme solution from the lens until normal intralenticular pressure is restored.

The composition of the digestive mixture and the intralenticular incubation time is adjusted to achieve a high level of liquefaction or softening of the lens nuclear and cortical region. Termination of the lens liquefaction process and protection of other intraocular structures, in the event of escape of the enzymatic digestive agent from the lens capsule, can be achieved by introduction of specific enzyme inhibitors into the anterior chamber 20 of the eye through the same cannula.

Contemplated for practice of this invention is introduction of enzyme inhibitors into the anterior chamber 28 of the eye in the event of enzyme leakage thereinto, or even as a precaution against such leakage. High molecular weight (or macromolecular) inhibitors will not permeate into the lens capsule, and therefore, do not interfere with the enzymatic digestion of the lens cortex and nucleus. Low molecular weight inhibitors can diffuse through the lens capsule and may be used to terminate enzymatic digestion, both external and internal to the lens itself.

Comment has been made above as to how commercially available gear can be modified for practice of this invention, and accordingly, the apparatus of this invention need only be illustrated diagrammatically, as is done in FIG. 4.

Referring now to FIG. 4, it can be seen that the mechanical assembly used for injection of the enzyme into the lens consists of three principal parts—precision liquid dispensing unit 50, distribution valve 32 and the microcannula 30. Each of these three components is described as follows.

The pneumatically, hydraulically, or mechanically driven precision liquid dispensor 50 may be an electronically actuated, ratchet drive microliter dispensing assembly, such devices being well known to the art and need not be discussed here. The distribution valve 32 is a miniature four-terminal port valve containing a two-channel 90° distribution plug 62 with channels 64, 66 machined to tight specification so as to prevent leakage.

Valve body 65 is correspondingly provided with four ports 67, 69, 71, 73 and is machined to fit plug 62 without leakage. The valve 32 and the components therein fill the port 73 and cannula 30 with a predetermined fixed volume of the enzyme (e.g., 1, 3 or 5 microliters). (As a practical matter, porting plug 74 has no separate volume because cannula 30 is extended through porting plug 74).

Channels 64, 66 are of predetermined volume which, desirably, is from 2–10 times the combined volume of port 73 and may for example each be ten microliters. Thus when plug 62 is rotated to place channels 64, 66 into the position shown in FIG. 4, enzyme solution drawn from reservoir 51 is pumped by dispenser 50, e.g., a metering microliter power syringe, through line 53 into channel 66, porting plug 74 and cannula 30. At the same time, filtered air or an inert gas flows from an inlet to port 67, through channel 64 and out by way of port 69. When the surgeon is ready to operate, the distribution plug 62 is then rotated through 180° replacing the channel 66 containing volume of enzyme solution, e.g., a 10 microliter volume, with the gas containing volume of channel 64. During delivery of enzyme solution to the lens dispenser 50 is driven forward, e.g., in one microliter pulse, gradually compressing the in-line air pocket inside channel 64 until the contents of port 73 and cannula 30 are cleared of enzyme solution. Further activation of dispenser 50 drives air out cannula 30 to produce the small gas bubbles that seal the needle tract of the cannula. Alternatively, air or other gas may be employed to pneumatically drive the in-line gas pocket that in turn forces enzyme solution out of cannula 30, for example by carrying out a 90° valve reversal, leaving gas inlet port 67 connected to port 73, then pneumatically driving through inlet port 67.

As is readily apparant, the combined volume of enzyme solution inside port 73 and cannula 30 is intended to be the quantity of enzyme required for operating on a lens, i.e., the dosage unit. The 2–10:1 by volume ratio of gas in the valve channel 64 to the dosage unit volume provides enough gas for the desired bubble, despite the compression that occurs as the gas pocket is forced through cannula 30 into the lens and enough gas for spacing purposes so that excess enzyme is not introduced into the lens after the bubble has been discharged from the cannula.

In any event, the enzyme solution pumped into lens 10 creates for itself a pocket which frequently is shaped like an open umbrella whose stem is the cannula track. The puncture opening made by the cannula constitutes a narrow channel capable of being sealed by the gas bubble, particularly when the cannula is partially withdrawn so that the gas is pumped directly into the cannula track. Experience (i.e., animal test studies) has indicated that the enzyme solution soon diffuses throughout the softer lens regions. Apparently, intra occular pressures are restored rather rapidly, without even initially, sufficient pressure being generated by the enzyme solution containing pocket to force the gas bubble out the cannula track.

If desired the enzyme solution dosage unit may be made small. The above procedure can then be repeated in a different region of the lens, for example, 2 × 3 microliter portions, instead of a 1 × 6 microliter dose. Introduction of multiple dosage units allows the surgeon to create an immediate distribution of enzyme solution throughout the lens.

If perchance a mishap occurs during the procedure, e.g., rupture of the posterier capsule, inhibitor can be introduced into the enzyme delivery system through port 67 and the plug 62 rotated appropriately to directly send the inhibitor through cannula 30 into the affected portion of the eye.

A suitable cannula is a 32 gauge stainless steel tube 8 inches long mounted in an appropriate porting plug 74 fitting which attaches to the distribution valve 32 at port 73. The outside diameter of the cannula is typically 0.009 inch and its internal holdup volume is less than 1 microliter. The most satisfactory needle point style is a short bevel 22° slant with an electronically tapered tip. Fittings available commercially are designed to have negligible dead volume and, therefore, variation in the volume of enzyme solution to be delivered is controlled by predetermining the holdup volume of the terminal port 73 of the distribution valve 32. The entire assembly may be presterilized, conveniently, cold sterilized by chemical means, then rinsed with a sterile solution before the enzyme solution is quickly loaded into the assembly, e.g., loading within 3 minutes. When competently handled the assembly herein described will reproducibly deliver a selected volume of enzyme solution into the lens with virtually no leakage into the anterior chamber.

The cannula described above is suitable for all lens types which have been encountered during test studies. The rabbit lens is approximately the consistency of a normal human cataract, and no difficulty has been experienced in making direct injections in the nuclear region of this type of lens. In the case of the cat which has an extremely dense nuclear region and in the tests on the hard bruescent human cataract, no difficulty has been observed in penetrating the nuclear region with this cannula. However, with extremely dense lens centers the enzyme is best placed in the more peripheral areas of the nucleus or softer cortical regions.

What is claimed:

1. An apparatus for introducing a predetermined dosage unit volume of enzyme solution into cataracts comprising:
   (a) a reservoir of enzyme solution and an enzyme solution delivering means therefrom
   (b) a source of gas
   (c) a multiport valve having therein at least four ports
   (d) a cannula said cannula, gas source and reservoir being each connected to a different valve port, the fourth valve port being an exhaust port, said valve having therein two channels connectable to said ports two by two with the gas source connecting to the exhaust port and the reservoir connecting to the cannula; and conversely, the gas source connecting to the cannula and the reservoir connecting to the exhaust port, the combined volume within said cannula and the valve port connected to the cannula being predetermined to correspond to a single dosage unit of enzyme solution, and the volume of each valve channel being greater than a single dosage unit, whereby enzyme solution may be delivered from said reservoir through one channel of said valve into the cannula, while gas passes from the gas source through the second channel of said valve to the exhaust port of said valve, then upon complete valve reversal interposing the gas containing second channel in line between enzyme reservoir and cannula, all gas trapped in said second channel by the valve reversal becomes a gaseous separator limiting continuous enzyme solution flow out the cannula to the single dosage unit volume already downstream of the gas trapped, and the source of gas for a gas bubble capable of sealing off the track made by cannula penetration into a cataract.

2. The apparatus of claim 1 wherein the ratio of the channel volume to that of the single dosage unit is in the range of 2–10 to 1.

3. The apparatus of claim 1 wherein the enzyme delivery means is interposed between enzyme solution reservoir and valve to draw enzyme solution from said reservoir and then force same downstream through valve and cannula.

4. A method of introducing single dosage units of enzyme solution into cataracts involving:
  (a) a reservoir of enzyme solution and an enzyme solution delivery means therefrom
  (b) a source of gas
  (c) a multiport valve having therein at least four ports
  (d) a cannula said cannula, gas source and reservoir being each connected to a different valve port, the fourth valve port being an exhaust port, said valve having therein two channels connectable to said ports two by two with the gas source connecting to the exhaust port and the reservoir connecting to the cannula, and conversely the gas source connecting to the cannula and the reservoir connecting to the exhaust port, the combined volume within said cannula and the valve port connected to the cannula being predetermined to correspond to a single dosage unit of enzyme solution, and the volume of each valve channel being greater than a single dosage unit, the method which comprises:
  (1) setting the valve to connect reservoir with cannula through one channel of said valve and then delivering enzyme solution from the reservoir through the valve to the cannula, filling the cannula with enzyme solution and passing gas from the gas source through the second channel of said valve to the exhaust port, thereafter
  (2) completely reversing the valve channels to interpose the second channel as the valve connection between enzyme reservoir and cannula, then
  (3) introducing the cannula into a cataract and delivering enzyme solution from the reservoir into the valve, forcing thereby gas trapped in said second channel by the valve reversal into the cannula, and in turn forcing enzyme solution already in the cannula into the cataract; and
  (4) discharging some gas through the cannula into the cataract forming thereby a gas bubble which seals against leakage of enzyme solution out of the lens through the cannula track therein.

5. The method of claim 4 wherein air is the gas.

6. The method of claim 4 including the step of partially withdrawing the cannula from the cataract before introducing gas into the cataract.

7. A method of introducing single dosage units of enzyme solution into cataracts involving:
  (a) a reservoir of enzyme solution and an enzyme solution delivery means therefrom
  (b) a source of gas
  (c) a multiport valve having therein at least four ports
  (d) a cannula said cannula, gas source and reservoir being each connected to a different valve port, the fourth valve port being an exhaust port, said valve having therein two channels connectable to said ports two by two with the gas source connecting to the exhaust port and the reservoir connecting to the cannula, and conversely the gas source connecting to the cannula and the reservoir connecting to the exhaust port, the combined volume within said cannula and the valve port connected to the cannula being predetermined to correspond to a single dosage unit of enzyme solution, and the volume of each valve channel being greater than a single dosage unit, the method which comprises:
  (1) setting the valve to connect reservoir with cannula through one channel of said valve and then passing enzyme solution from the reservoir through the valve to the cannula filling the cannula with enzyme solution and passing gas from the gas source through the second channel of said valve to the exhaust port, thereafter
  (2) shifting the valve channels to interconnect the gas source and cannula, and
  (3) introducing the cannula into a cataract and passing gas through the valve, forcing thereby the gas into the cannula, and the enzyme solution already in the cannula into the cataract; and
  (4) discharging some gas through the cannula into the cataract forming thereby a gas bubble which seals against leakage of enzyme solution out of the lens through the cannula track therein.

8. The method of claim 7 wherein air is the gas.

9. The method of claim 7 including the step of partially withdrawing the cannula from the cataract before introducing gas into the cataract.

* * * * *